United States Patent [19]

Antonucci et al.

[11] Patent Number: 5,037,473

[45] Date of Patent: Aug. 6, 1991

[54] DENTURE LINERS

[76] Inventors: Joseph M. Antonucci, 4608 Frankin St., Kensington, Md. 20895; Robert E. Müller, 88 Abbotsford Rd., Winnetka, Ill. 60093

[21] Appl. No.: 339,802

[22] Filed: Apr. 18, 1989

Related U.S. Application Data

[63] Continuation of Ser. No. 122,197, Nov. 18, 1987, abandoned.

[51] Int. Cl.$^5$ .................... A61C 13/23; A61K 6/00
[52] U.S. Cl. .................... 106/35; 260/998.11; 433/168.1; 433/217.1; 523/109; 523/118; 523/120
[58] Field of Search ............ 106/35; 433/217.1, 168.1; 523/109, 115, 116, 117, 118, 120; 260/998.11

[56] References Cited

U.S. PATENT DOCUMENTS

| | | | |
|---|---|---|---|
| 3,446,875 | 5/1969 | Bruckmann | 523/115 |
| 3,969,303 | 7/1976 | Prosen | 523/120 |
| 4,001,939 | 1/1977 | Gross | 523/115 |
| 4,150,485 | 4/1979 | Lee, Jr. | 523/115 |
| 4,459,193 | 7/1984 | Ratcliffe | 523/115 |
| 4,490,497 | 12/1984 | Evrard | 523/116 |
| 4,515,910 | 5/1985 | Rawls et al. | 523/116 |
| 4,536,523 | 8/1985 | Antonucci | 523/115 |
| 4,572,920 | 2/1986 | Rawls et al. | 523/115 |
| 4,670,480 | 6/1987 | Morrone | 523/116 |
| 4,674,980 | 6/1987 | Ibsen et al. | 523/116 |
| 4,781,940 | 11/1988 | Denton, Jr. | 523/116 |

FOREIGN PATENT DOCUMENTS 323120 7/1989 European Pat. Off. .
329268 8/1989 European Pat. Off. .

*Primary Examiner*—Paul Lieberman
*Assistant Examiner*—Linda D. Skaling
*Attorney, Agent, or Firm*—Fitch, Even, Tabin & Flannery

[57] ABSTRACT

A denture liner composition is provided comprising a methacrylate polymer and/or copolymer in powder form to be wetted by a liquid composition containing dimethacrylate, butyl methacrylate, and long chain methacrylate monomers, the mixture setting upon wetting and being polymerized by visible light and chemical action. A method for using the composition in denture liner formation is also provided.

8 Claims, No Drawings

DENTURE LINERS

This is a continuation of application Ser. No. 122,197, filed Nov. 18, 1987, now abandoned.

The present invention relates generally to dentures, and more particularly, it relates to the relining of dentures by use of particular compounds.

BACKGROUND OF INVENTION

Many dentures require taking a new impression of the mouth and relining to result in better fitting dentures. Changes in the mouth tissue and distortion of the size and shape of the prosthesis cause dentures to loosen and become uncomfortable for the patient.

Usual relining procedures require taking a new impression of the patient's mouth and sending it, with the denture, to a dental laboratory where it is relined. This normally takes at least one day. Many patients are reluctant to be without their denture even for one meal or overnight. Such patients usually resort to chairside procedures or do-it-yourself denture liners which only provide temporary relief. Several premixed or powder/liquid materials have been introduced for chairside use. With these reline systems, the dentist is able to reline the denture with the patient in the chair and cure the denture chairside by means of a visible light source. The prime objections to the use of these materials have been that the premixed materials are too stiff to obtain an accurate impression, or are too soft to maintain the impression, or are not fully cured by the visible light. Any one of these problems can result in an unsatisfactory denture liner.

Other denture liner formulations (premixed or powder/liquid) of impression quality with a chairside procedure offer only temporary relief for the patient. Many of these reline materials are adversely affected by the oral environment with softening and staining. Further, prior formulations would set up in the mouth and become so rigid as to be difficult to remove and cause distortion of the impression.

A principal object of this invention is to provide an improved denture liner composition.

A further object of this invention is to provide a denture liner composition which will set up in the mouth but have such resiliency as to be removable without distortion of the impression and curable to a hard condition.

A still further object of the invention is the provision of a denture composition which is readily cured by visible light.

Another object is the provision of an improved denture composition which can exist in the oral environment without significant softening and/or staining.

GENERAL DESCRIPTION

A hydrophobic composition has been developed which can be mixed as a powder and liquid (or premix) to a fluid consistency similar to a conventional impression material. After the denture has had the palate surface and peripheral border areas ground with a carbide burr to remove plaque and objectional areas, the impression mix is placed into the denture. The prosthesis is then placed into the patient's mouth and held at the correct position for several minutes to permit the material to stiffen enough so that upon removal from the mouth it will maintain the desired new impression. The relined denture is then placed under a visible light source for 3-15 minutes. The formulation may be polymerized with visible light alone, but preferably polymerization is effected with a dual polymerization system or hardening mechanism which permits polymerization with the visible light from the outside and an auto-catalyzed or chemical system from the inside. This dual system assures a complete cure or polymerization of the denture liner to a hard condition. Thick areas of the liner where penetration of the visible light is insufficient could result in areas removed from the surface to still be not completely polymerized. In order to assure a complete hardening or polymerization of the surface of the denture liner, an air barrier coating, such as mineral oil, is applied to the surface of the denture liner to permit a complete polymerization in the absence of air while curing with a visible light source. After polymerization, the relined denture is then ground with a carbide burr to remove any excess material from the peripheral border and cleaned with water and a detergent before returning the denture to the patient's mouth.

The improved denture liner composition of the invention is provided from a powder part and a liquid part, the powder part being from about six parts to one part of powder to one part of liquid. The respective powder part and liquid part have the following formations:

Powder Part:

Methacrylate polymers and/or copolymers, such as poly (ethyl methacrylate) or copolymers of ethyl methacrylate and methyl methacrylate unfilled or filled with fumed silica, calcium-sodium metaphosphate, micro glasses or other inorganic or organic materials mixed with 0.5-1.0% benzoyl peroxide or similar chemical initiator.

Liquid Part:
10-80% Bisphenol a dimethacrylate or ethoxylated bisphenol a dimethacrylate or urethane dimethacrylate
10-50% n-Butyl or iso-butyl methacrylate monomer
10-40% Lauryl methacrylate, stearyl methacrylate, iso-bornyl methacrylate or methacrylate monomers with 6-20 carbons in chain length.
0-95% Dimethyl maleate, diethyl maleate, dibutyl fumarate or other polymerizable platicizers
0.2-1.0% N,N-dimethyl toluidine or like chemical activator
0.1-0.5% Camphorquinone, benzil or like diketones or visible light initiators
0.2-1.0% 4-ethyl N, N-dimethyl amino benzoate or like light and/or chemical activators All percentages are by weight.

The initial stiffening of the mix in the mouth to maintain the desired impression in the relined denture is a result of butyl methacrylate or like monomer wetting the powder part comprising polyethyl methacrylate polymer or ethyl methacrylate/methyl methacrylate copolymer. The particle size of the polymer powder part to achieve the desired wetting has been found to be critical and should be in the range of 5 microns to 100 microns. Absent this wetting, the composition does not satisfactorily set.

The chemical or auto-catalyzed cure or polymerization is controlled by the amount of benzoyl peroxide or similar catalyst or initiator and the amount of the N,N-dimethyl toluidine or similar chemical activator.

The visible light cure or polymerization is controlled by the amount of camphorquinone or similar visible light initiator, the amount of the 4-Ethyl N,N-dimethyl amino benzoate or similar light activator and the visible light source. A visible light source of 350-550 nanometers has been found to be the most effective light range.

Long chain (6-20 carbon atoms) monomers such as lauryl methacrylate, stearyl methacrylate or iso-bornyl methacrylate have been shown to impart added toughness to any of the mixes.

Polymerizable plasticizers such as diethyl maleate or dibutyl fumarate will impart softness to any of these formulations with the degree of softness directly proportional to the amount of plasticizer included in the denture reliner formulation.

The mixture of powder part and liquid part should upon wetting of the powder part in the mouth cause setting of the denture liner while allowing it to be flexible to be removed from the mouth, and particularly from undercuts, and yet be resilient enough to maintain the accuracy of the impression. In accord with the invention, this is achieved in part by the powder size being in the desired range.

SPECIFIC EXAMPLES

EXAMPLE I

| | |
|---|---|
| 4 parts by weight powder | Copolymer comprising 50% methyl methacrylate 50% ethyl methacrylate, and 0.5% benzoyl peroxide |
| 1 part by weight liquid | 100% Urethane monomer 0.2% N,N-dimethyl toluidine 0.3% Camphoroquinone 0.5% Ethyl N-N dimethyl amino benzoate |

EXAMPLE II

| | |
|---|---|
| 3 parts by weight powder | Copolymer 25% methyl methacrylate 75% ethyl methacrylate 0.2% Benzoyl peroxide |
| 1 part by weight liquid | 75% Bisphenol a dimethacrylate 25% Ethylene glycol dimethacrylate 0.5% Camphoroquinone 0.5% 4-Ethyl N-N-dimethyl amino benzoate |

EXAMPLE III

| | |
|---|---|
| 2 parts by weight powder | Copolymer 10% methyl methacrylate 90% Ethyl methacrylate 1.0% Benzoyl peroxide |
| 1 part by weight liquid | 80% Ethoxylated bisphenol a dimethacrylate 20% Iso-bornyl methacrylate monomer 0.3% Camphoroquinone 0.4% 4-Ethyl N,N-dimethyl amino benzoate |

EXAMPLE IV

| | |
|---|---|
| 1.5 parts by weight powder | Ethyl methacrylate Polymer 0.5% Benzoyl peroxide |
| 1 part by weight liquid | 50% Ethoxylated bisphenol a dimethacrylate 40% n-Butyl methacrylate monomer 10% Lauryl methacrylate monomer 0.5% N, N-dimethyl toluidine 0.2% Camphorquinone 0.5% 4-Ethyl N,N-dimethyl amino benzoate |

EXAMPLE V

| | |
|---|---|
| 1 part by weight powder | Copolymer 90% methyl methacrylate 10% Ethyl methacrylate 0.2% Benzoyl peroxide |
| 1 part by weight liquid | 40% Ethoxylated bisphenol a dimethacrylate 20% Iso-butyl methacrylate monomer 10% Stearyl methacrylate monomer 30% Diethyl maleate 0.5% N,N-dimethyl toluidine 0.3% Camphoroquinone 0.4% 4-Ethyl N,N-dimethyl benzoate |

The composition of each of the Examples was used on dentures and applied in patient's mouths. In each case, the denture liner set up in the mouth to form an impression and was removed from the gums, including undercuts, and maintained an accurate impression. The denture liners were cured under visible light to form a hard and lasting lined denture which could withstand the mouth environment.

Various inorganic and/or organic fillers may be added to the formulations of any of the above Examples to result in desired physical properties or to give thixoptopy to the mix.

The various features of the invention which are believed to be new are set forth in the following claims:

What is claimed is:

1. A polymerizable composition for relining dentures comprising:
   a powder part comprising a methacrylate polymer selected from the group consisting of polymers of methyl methacrylate, ethyl methacrylate and mixtures thereof and benzoyl peroxide as a chemical initiator; and a liquid part comprising a dimethacrylate monomer, a butyl methacrylate monomer, a long chain methacrylate monomer having a chain length of from 6 to 20 carbons, a polymerizable plasticizer, N,N-dimethyl toluidine as a chemical activator, a visible light initiator selected from the group consisting of camphoroquinone, benzyl and mixtures thereof and 4 ethyl N,N-dimethyl amino benzoate as a combined light and chemical initiator, wherein said powder part contains 10 to 99.5% by weight of said methacrylate polymer and 0.5 to 9.0% by weight of said chemical initiator, and said liquid part contains 10 to 80% by weight of said dimethyacrylate monomer, 10 to 50% by weight of said butyl methacrylate monomer, 10 to 40% by weight of said long chain methacrylate monomer, 0 to 69.5% by weight of said polymerizable plasticizer, 0.2 to 1.0% by weight of said chemical activator, 0.1 to 0.5% by weight of said visible light initiator and 0.2 to 1.0% by weight of said combined light and chemical initiator.

2. A composition according to claim 1 wherein said powder part further comprises inorganic or organic filler materials or mixtures thereof.

3. A compound according to claim 1 wherein said dimethacrylate monomer in said liquid part is selected from the group consisting of bisphenol a dimethacrylate, ethoxylated bisphenol dimethacrylate monomer, urethane dimethacrylate, and mixtures thereof.

4. A composition according to claim 1 wherein said butyl methacrylate monomer in said liquid part is selected from the group consisting of n-butyl methacrylate monomer, iso-butyl methacrylate monomer, and mixtures thereof.

5. A composition according to claim 1 wherein said long chain methacrylate monomer in said liquid part is selected from the group consisting of lauryl methacrylate monomer, stearyl methacrylate monomer, iso-bornyl methacrylate monomer, and mixtures thereof.

6. A composition according to claim 1 wherein said polymerizable plasticizer in said liquid part is selected from the group consisting of dimethyl maleate, diethyl maleate, dibutyl fumarate, and mixtures thereof.

7. A composition according to claim 2 wherein said inorganic filler materials are selected from the group consisting of fumed silica, calcium-sodium metaphosphate, micro glasses, and mixtures thereof.

8. A composition according to claim 1 wherein the particle size of the said powder part is between about 5 microns and about 100 microns.

* * * * *